United States Patent
Dohi et al.

(10) Patent No.: US 7,222,518 B2
(45) Date of Patent: May 29, 2007

(54) TRANSFORMER MONITORING SYSTEM

(75) Inventors: Manabu Dohi, Chiba (JP); Toshiki Shirahata, Chiba (JP); Takayiki Kondo, Chiba (JP)

(73) Assignee: Hitachi Industrial Equipment Systems Co., Ltd., Chiba (JP)

( * ) Notice: Subject to any disclaimer, the term of this patent is extended or adjusted under 35 U.S.C. 154(b) by 0 days.

(21) Appl. No.: 11/417,413

(22) Filed: May 3, 2006

(65) Prior Publication Data

US 2006/0201264 A1 Sep. 14, 2006

Related U.S. Application Data

(63) Continuation of application No. 10/896,097, filed on Jul. 20, 2004, now Pat. No. 7,140,237.

(30) Foreign Application Priority Data

Apr. 7, 2004 (JP) .............................. 2004-112651

(51) Int. Cl.
    G00N 11/00 (2006.01)
(52) U.S. Cl. .................................. 73/53.01
(58) Field of Classification Search ............... 73/53.01, 73/865.9
    See application file for complete search history.

(56) References Cited

U.S. PATENT DOCUMENTS

| | | | |
|---|---|---|---|
| 2,298,229 A * | 10/1942 | Putman et al. ................. 361/37 |
| 4,148,086 A * | 4/1979 | Landa et al. ................... 361/37 |
| 4,654,806 A | 3/1987 | Poyser et al. |
| 6,177,803 B1 * | 1/2001 | Train et al. .................. 324/552 |
| 6,393,895 B1 * | 5/2002 | Matsiev et al. ............ 73/24.06 |
| 6,446,027 B1 * | 9/2002 | O'Keeffe et al. ........... 702/183 |
| 6,609,079 B1 | 8/2003 | Seitlinger |
| 6,853,939 B2 * | 2/2005 | Coffeen ....................... 702/108 |
| 6,906,630 B2 * | 6/2005 | Georges et al. ............. 340/646 |
| 7,140,237 B2 * | 11/2006 | Dohi et al. ................. 73/53.01 |
| 2004/0057491 A1 * | 3/2004 | Stenestam ..................... 374/29 |

FOREIGN PATENT DOCUMENTS

| JP | 05-227644 | 9/1993 |
|---|---|---|
| JP | 08-213246 | 8/1996 |

* cited by examiner

*Primary Examiner*—Hezron Williams
*Assistant Examiner*—Rodney Frank
(74) *Attorney, Agent, or Firm*—Townsend and Townsend and Crew LLP

(57) ABSTRACT

An oil-filled transformer monitoring system is provided which calculates an oil temperature of an oil-filled transformer with high precision from a current of the transformer and an ambient temperature. The oil-filled transformer monitoring system of this invention has an oil temperature calculation device to calculate a transformer oil temperature using measurements from a transformer current measuring device and an ambient temperature measuring device. The transformer monitoring system also has an oil temperature measuring device and compares an output value from the oil temperature calculation device with an output value from the oil temperature measuring device to detect any anomaly.

3 Claims, 4 Drawing Sheets

TRANSFORMER MONITORING SYSTEM

CLAIM OF PRIORITY

This application is a continuation of U.S. patent application Ser. No. 10/896,097, filed Jul. 20, 2004, now U.S. Pat. No. 7,140,237, entitled "Transformer Monitoring System," which claims priority from Japanese application JP 2004-112651, filed on Apr. 7, 2004, each of which is hereby incorporated herein by reference.

BACKGROUND OF THE INVENTION

The present invention relates to a monitoring of a state of oil-filled transformers using information such as transformer oil temperature, current and ambient temperature.

A stable supply of electricity is important and it is therefore necessary to periodically monitor transformers to forestall possible failures. For this purpose, monitoring a voltage, current and oil temperature of the transformers is effective. The monitoring of the oil temperature generally involves estimating an oil temperature from an average load factor, visually checking a temperature reading on a thermometer, comparing the estimated oil temperature with the temperature reading on the thermometer to decide whether the transformer in question is normal or not, and at the same time checking if the temperature reading on the thermometer has exceeded a predetermined value.

Another practice involves the use of a thermometer with an alarm contact which issues an alarm for detection of an anomaly when the oil temperature exceeds a set temperature.

Another method of monitoring is disclosed, for instance, in JP-A-5-227644 which, when determining a remaining service life from a maximum winding temperature, calculates an oil temperature rise and determines an oil temperature by adding a measured ambient temperature to the oil temperature rise.

In another method disclosed in JP-A-8-213246, a means is provided that calculates a transformer oil temperature from a reading on a thermometer attached to the outside of a case of the oil-filled transformer and from a measured load factor of the transformer.

In the above conventional method using a visual check, however, since an oil temperature change lags load factor and ambient temperature changes, checking the measured temperature after the load factor or ambient temperature has changed cannot easily determine if it is a proper temperature or not.

Further, JIS C 4304 specifies that a limit of an oil temperature rise is 50K at maximum during the rated load operation and that the transformer can be used in an ambient temperature range of between −20° C. and 40° C. Thus, to precisely estimate the oil temperature requires considering influences of ambient temperature.

When the oil temperature exceeds the set temperature of the thermometer with an alarm contact, an alarm is issued for detection of an anomaly. However, since the oil temperature is a sum of a temperature rise caused by a transformer loss and a temperature rise caused by the ambient temperature, if the ambient temperature is low, the oil temperature will not reach the set temperature even during an overload operation. Further, even when the transformer is used below the rated load, an alarm may be issued if the ambient temperature is high and the set temperature is exceeded. This method therefore could not decide whether the oil temperature is correct or not.

Nor can the conventional monitoring system determine if the oil temperature is correct or not.

Further, since the above conventional technique uses a measured value for the ambient temperature in determining the maximum winding temperature, the fact is not taken into account that an oil temperature change lags behind an ambient temperature change.

Further, since the conventional technique does not consider ambient temperature variations when indirectly measuring the oil temperature from the case outer surface temperature, an error occurs between the measured value and the converted value if the ambient temperature changes sharply. Moreover, when the converted value is based on a case measured value, which indirectly measures the oil temperature, since the measured value constitutes a reference, it is not possible to estimate accurately what the true oil temperature is.

Therefore, if an abnormal condition occurs in connected portions of circuit within coil and case as a result of progressive degradations over time or vibrations caused by earthquakes, oil is heated and its temperature rises. However, since the true oil temperature cannot be estimated accurately, it is not possible to decide that an abnormal condition has occurred inside the transformer.

SUMMARY OF THE INVENTION

It is an object of the present invention to provide a transformer monitoring system which can solve the aforementioned problems experienced with conventional systems and which can calculate with high precision an oil temperature of an oil-filled transformer from an ambient temperature and a transformer current, monitor the oil-filled transformer by using the calculated oil temperature and a measured oil temperature of the transformer, and also monitor an inner pressure and voltage.

To achieve the above objective, the transformer monitoring system of this invention comprises: a current measuring means to measure a current in an oil-filled transformer; an ambient temperature measuring means; an oil temperature calculation means to calculate an oil temperature of the oil-filled transformer using measurements from the current measuring means and the ambient temperature measuring means; an oil temperature measuring means to measure the oil temperature of the oil-filled transformer; a comparison means to compare the calculated oil temperature and the measured oil temperature; and an oil temperature anomaly decision means to decide that there is an abnormal condition when a difference between the calculated oil temperature and the measured oil temperature exceeds a set value.

The transformer monitoring system also has an inner pressure measuring means and an inner pressure anomaly decision means to check an inner pressure value obtained from the inner pressure measuring means to decide whether the inner pressure is abnormal or not.

The transformer monitoring system also includes a voltage measuring means and a voltage anomaly decision means to check a voltage value obtained from the voltage measuring means to decide whether the voltage is abnormal or not.

Other objects, features and advantages of the invention will become apparent from the following description of the embodiments of the invention taken in conjunction with the accompanying drawings.

DETAILED DESCRIPTION OF THE INVENTION

A system for monitoring an oil-filled transformer as one embodiment of this invention will be described by referring to the accompanying drawings.

Figure 1:
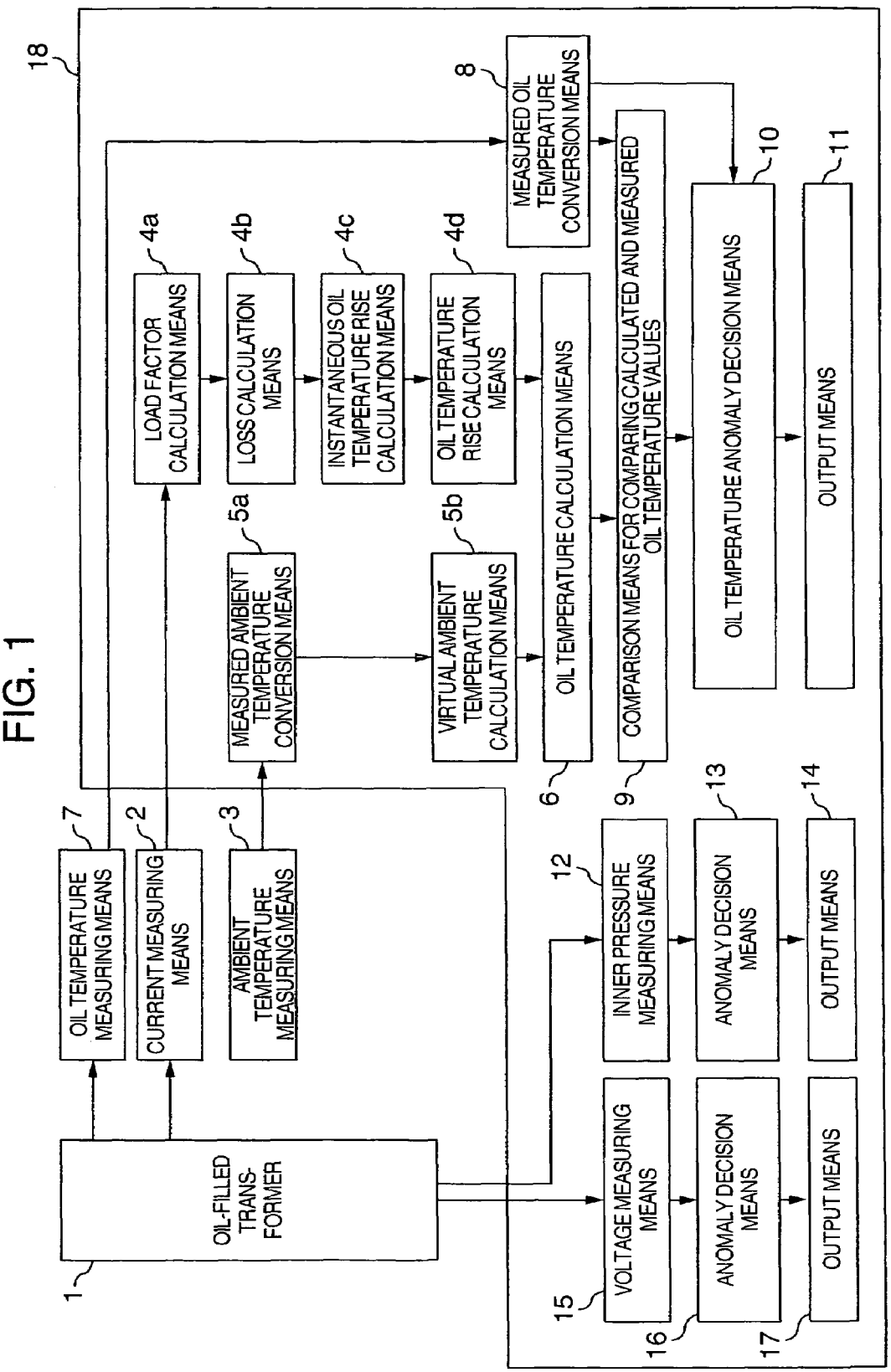
FIG. 1 is a block diagram of an oil-filled transformer monitoring system.

FIG. 1 is a block diagram of an oil-filled transformer monitoring system.

In FIG. 1, reference number 1 represents an oil-filled transformer; 2 a current measuring means constructed of a current transformer (CT) for metering current of the transformer; 3 an ambient temperature measuring means constructed of a temperature measuring resistor (search coil) for measuring an ambient temperature; 4a a load factor calculation means for calculating a load factor from a signal output from the current measuring means 2; 4b a loss calculation means for calculating a loss from a result produced by the load factor calculation means 4a; 4c an instantaneous oil temperature rise calculation means for calculating an instantaneous oil temperature rise from a result produced by the loss calculation means 4b; 4d an oil temperature rise calculation means for calculating an oil temperature rise from a result produced by the instantaneous oil temperature rise calculation means 4c; 5a a measured ambient temperature conversion means for converting an output signal from the ambient temperature measuring means 3 into an ambient temperature measured value; 5b a virtual ambient temperature calculation means for calculating a virtual ambient temperature from a result produced by the measured ambient temperature conversion means 5a; 6 an oil temperature calculation means for calculating an oil temperature from the oil temperature rise calculation means 4d and the virtual ambient temperature calculation means 5b; 7 an oil temperature measuring means constructed of a temperature measuring resistor (search coil) to measure the actual oil temperature in a tank of the transformer; 8 a measured oil temperature conversion means for converting an output from the oil temperature measuring means 7 into an oil temperature measured value; 9 a comparison means for comparing a calculated oil temperature value from the oil temperature calculation means 6 and a measured oil temperature from the measured oil temperature conversion means 8; 10 an oil temperature anomaly decision means for deciding that the oil temperature is abnormal when a difference between the calculated oil temperature value and the measured value exceeds a set value and for checking if the result produced by the measured oil temperature conversion means 8 is in excess of an oil temperature upper limit set value; 11 an output means for outputting an anomaly signal when the oil temperature anomaly decision means 10 decides that the oil temperature is abnormal; 12 an inner pressure measuring means constructed a pressure sensor to measure an inner pressure in the oil-filled transformer tank; 13 an anomaly decision means for converting a signal from the inner pressure measuring means 12 into a pressure and checking if the calculated inner pressure is in excess of an upper limit set value; 14 an output means for outputting an anomaly signal when the inner pressure anomaly decision means 13 decides that the inner pressure is abnormal; 15 a voltage measuring means constructed of a voltage transformer (VT) to measure a voltage of the transformer; 16 an anomaly decision means for converting a signal from the voltage measuring means 15 into a voltage and checking if the converted voltage is in excess of an upper limit set value and also if it is less than a lower limit set value; and 17 an output means for outputting an anomaly signal when the voltage anomaly decision means 16 decides that the voltage is abnormal.

Next, by referring to the system block diagram of FIG. 1, how signals are produced and processed at various parts with elapse of time will be explained.

Figure 2:
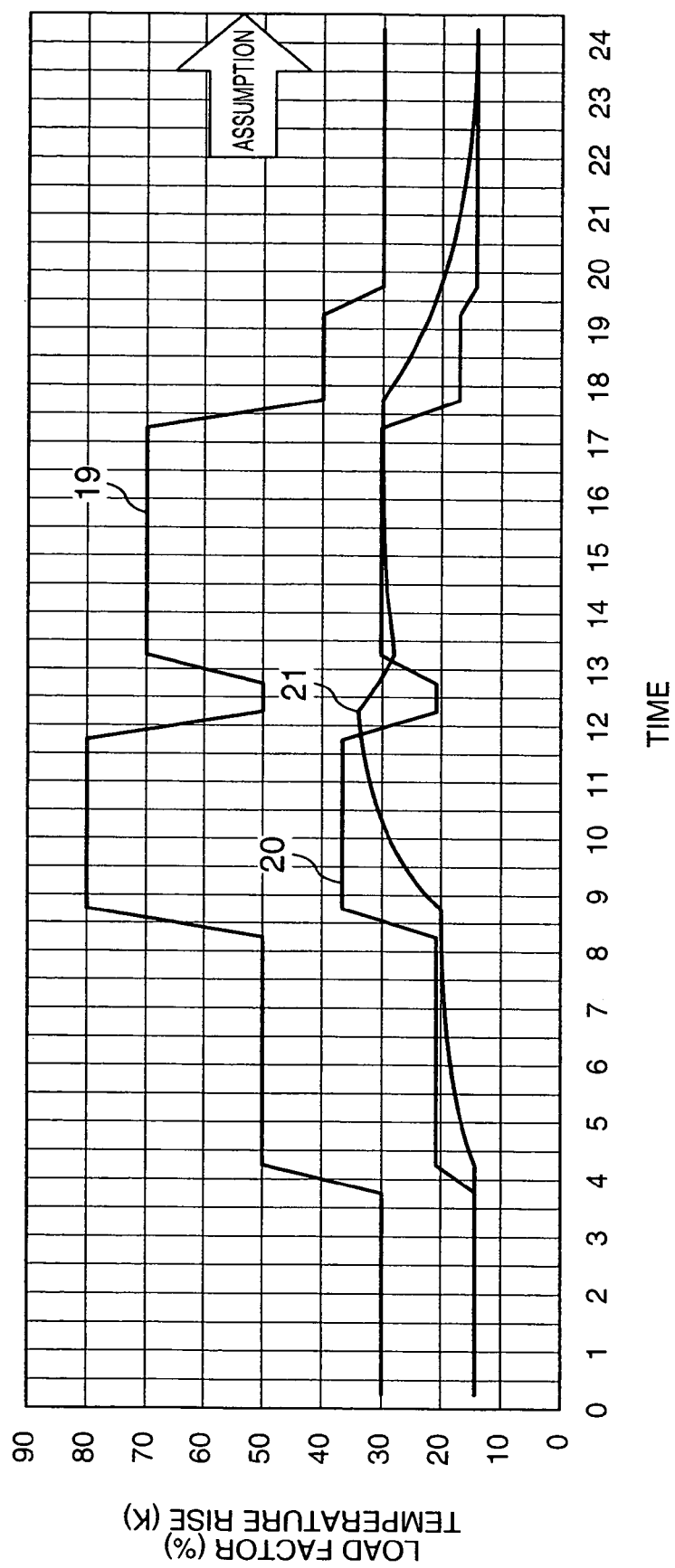
FIG. 2 is a graph showing an instantaneous oil temperature rise when a load factor of the oil-filled transformer changes and an oil temperature rise converted value.

FIG. 2 shows a load factor 19, an instantaneous oil temperature rise 20 and an oil temperature rise converted value 21 for the oil-filled transformer in this embodiment. The load factor 19 of the oil-filled transformer is calculated from an output signal from the current measuring means 2 of FIG. 1 by the load factor calculation means 4a. The instantaneous oil temperature rise 20 is calculated from the load factor 19 of the oil-filled transformer by the instantaneous oil temperature rise calculation means 4c. The instantaneous oil temperature rise 20 is further processed by the oil temperature rise calculation means 4d to determine the oil temperature rise converted value 21.

Figure 3:
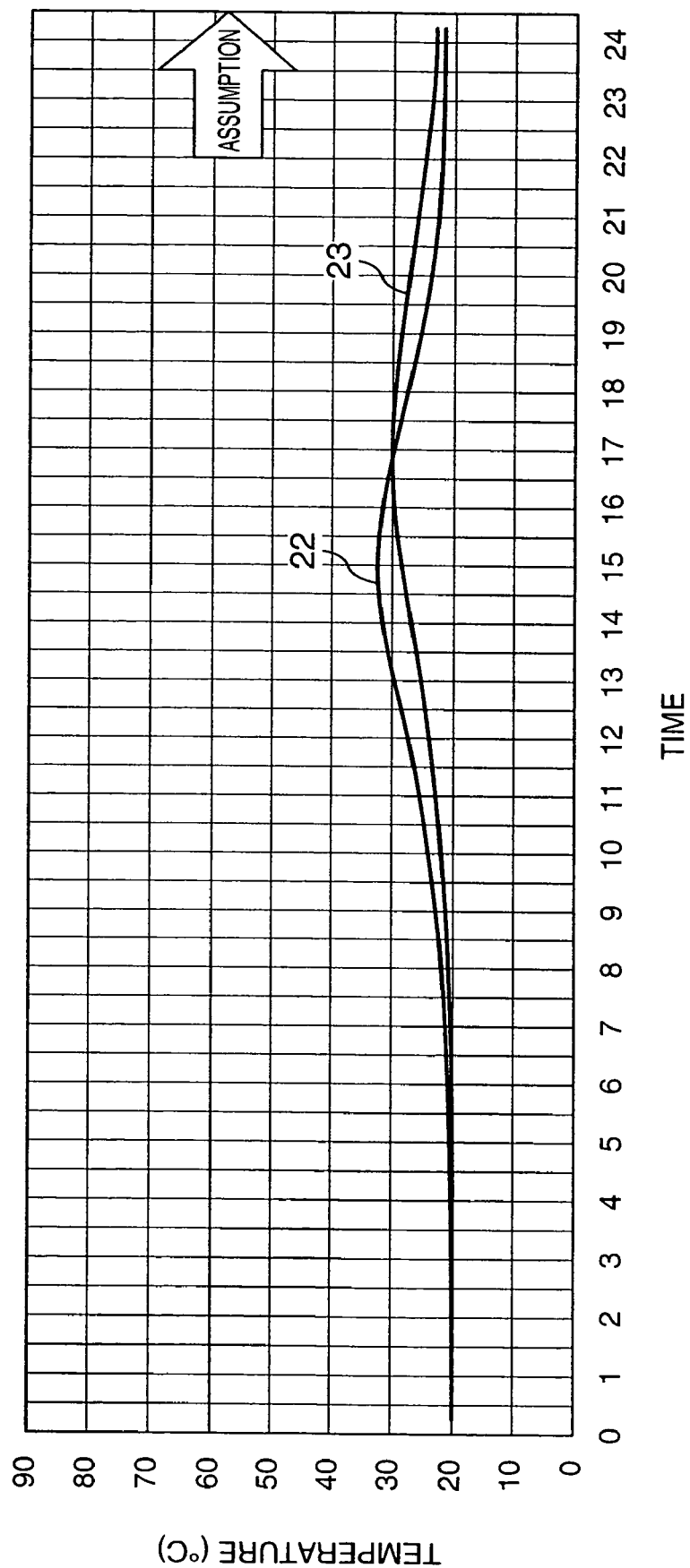
FIG. 3 is a graph showing an ambient temperature when the ambient temperature of the oil-filled transformer changes and a virtual ambient temperature.

FIG. 3 shows an ambient temperature 22 of the oil-filled transformer of this embodiment as it changes and a virtual ambient temperature 23 converted from the ambient temperature 22. The ambient temperature 22 is an output signal from the measured ambient temperature conversion means 5a and the virtual ambient temperature 23 is obtained by processing the ambient temperature 22 by the virtual ambient temperature calculation means 5b.

Figure 4:
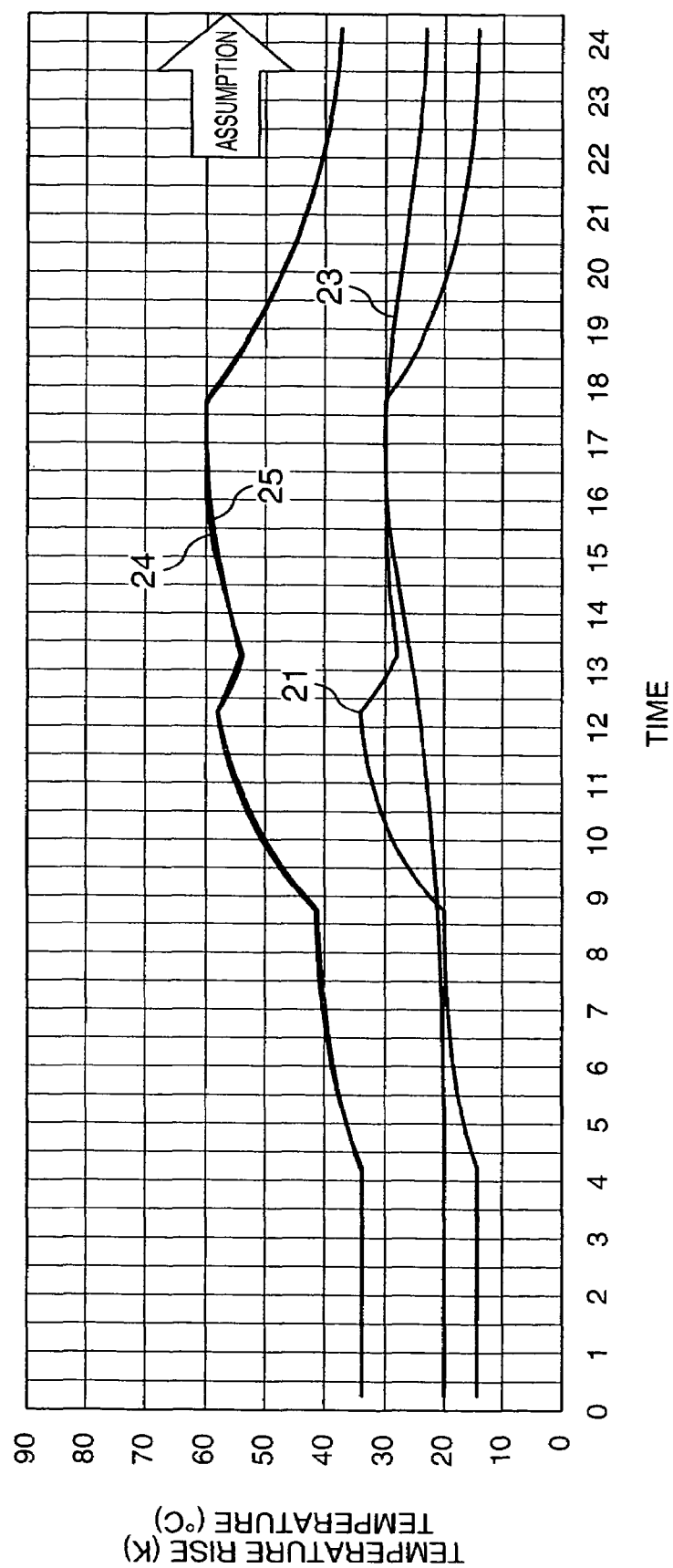
FIG. 4 is a graph showing an oil temperature rise of the oil-filled transformer, a virtual ambient temperature, an oil temperature converted value, and a measured oil temperature.

FIG. 4 shows an oil temperature converted value 24 for the oil-filled transformer of this embodiment, which is a sum of the oil temperature rise converted value 21 and the virtual ambient temperature 23. FIG. 4 also shows a measured oil temperature 25 of the oil-filled transformer.

It is seen from FIG. 4 that the oil temperature converted value 24 obtained from the current of the oil-filled transformer and the ambient temperature shows a good agreement with the measured oil temperature 25 and that the oil temperature is converted highly precisely.

In this system, if an abnormal condition occurs in connected portions of circuit such as terminals, as a result of progressive degradations over time or vibrations caused by earthquakes, and a contact resistance increases, a difference occurs between the oil temperature converted value 24 and the measured oil temperature 25 since the current flowing on the secondary side normally does not change.

This means it is possible to calculate the difference between the converted value and the measured value of the oil temperature by the comparison means 9 in the system block diagram of FIG. 1 and, if the difference is greater than a set value, to output a signal to an output means to issue an alarm annunciating the anomaly. It is also possible to set a desired load factor and ambient temperature and thereby estimate how the oil temperature will change. If it is found that the oil temperature is about to exceed the set upper limit temperature, it is possible to change the load or switch it to other power system in advance. Alternatively, ventilation may be performed to lower the ambient temperature in advance.

Next, a process of calculation performed by the monitoring system of FIG. 1 will be explained.

Let the oil temperature converted value 24 output from the oil temperature calculation means 6 be θoc(t). It is expressed as follows:

$$\theta oc(t) = \theta_{Ai}(t) + \theta mi(t) \qquad (1)$$

where θoc(t) [° C.] is an oil temperature t minutes later.

In the above equation (1), $\theta_{Ai}(t)$ represents a virtual ambient temperature of FIG. 2 and FIG. 3 and θmi(t) represents an oil temperature rise converted value shown in FIG. 1 and FIG. 3.

The virtual ambient temperature $\theta_{Ai}(t)$ and the oil temperature rise converted value θmi(t) are expressed as follows:

$$\theta_{Ai}(t) = \sum_{T=0}^{T=n} \left( \left\{ 1 - e^{-\left[\frac{(T)\times t}{T_A}\right]} \right\} - \left\{ 1 - e^{-\left[\frac{(T+1)\times t}{T_A}\right]} \right\} \right) \times \theta_A(-Tt) \qquad (2)$$

where $T_A$ [minutes] is a time constant of an oil temperature with respect to the ambient temperature, $\theta_A(-nt)$ [° C.] is an ambient temperature nxt minutes earlier, t [minutes] is a monitoring interval, and n is the number of past measurements used for calculation.

$$\theta mi(t) = \sum_{T=0}^{T=n} \left( \left\{ 1 - e^{-\left[\frac{(T)\times t}{Tm}\right]} \right\} - \left\{ 1 - e^{-\left[\frac{(T+1)\times t}{Tm}\right]} \right\} \right) \times \theta mu(-Tt) \qquad (3)$$

where Tm [minutes] is a time constant of an oil temperature with respect to a total loss and θmu(−nt) [K] is an oil temperature rise nxt minutes earlier in a steady state at a load factor of m %.

The oil temperature rise θmu(−nt) is the instantaneous oil temperature rise 20 of FIG. 2 and expressed as follows.

$$\theta mu(-nt) = \theta ou \times \left[ \frac{Wi + Wc \times \left(\frac{m(-nt)}{100}\right)^2}{Wi + Wc} \right]^k \qquad (4)$$

where θou [K] is an oil temperature rise in a steady state at a rated (100%) load, m(−nt) [%] is an instantaneous load factor nxt minutes earlier, Wi [W] is a no-load loss, Wc [W] is a load loss at the rated (100%) load, and k is a constant.

The instantaneous load factor m(−nt) is expressed as follows.

$$m(-nt) = \frac{i(-nt)}{Is} \times 100(\%) \qquad (5)$$

where I(−nt) [A] is a secondary instantaneous current nxt minutes earlier and Is [A] is a secondary rated current.

The secondary rated current is expressed as follows.

$$Is = \frac{P}{Es} \times \frac{1}{\sqrt{F}} \qquad (6)$$

where Es [V] is a secondary rated voltage, P [kVA] is a transformer rated capacity, F [phase] is the number of transformer phases, and t is an interval of measurement.

Performing calculations on the above equations (6) to (1) based on the service voltage and the specifications of the transformer results in the oil temperature converted value 24 as shown in FIG. 4, which is a close approximation to the measured oil temperature 25.

With this invention, since the oil temperature of the oil-filled transformer can be estimated with high precision, it is possible to predict an oil temperature change by assuming an appropriate load factor and ambient temperature. Therefore, if the oil temperature is expected to exceed a set value, the load can be changed or switched to other power system in advance. Other countermeasures can be taken in advance, such as performing ventilation to lower the ambient temperature.

Further, if an abnormal condition occurs in connected portions of circuit within coil and case as a result of progressive degradations over time or vibrations caused by earthquakes, the anomaly in the transformer, such as abnormal voltage and abnormal inner pressure, can be detected immediately, contributing greatly to the supervision of the oil-filled transformer.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A transformer monitoring system comprising:
    a current measuring means to measure a current flowing in an oil-filled transformer;
    an ambient temperature measuring means to measure an ambient temperature;
    an oil temperature calculation means to calculate an oil temperature in the oil-filled transformer from measurements of the current measuring means and the ambient temperature measuring means; and
    an oil temperature abnormal decision means to obtain an oil temperature converted value by calculations on a sixth equation, a fifth equation, a fourth equation, a third equation, a second equation, and a first equation based on a voltage and specifications of the transformer, and to compare the oil temperature converted value with an output value from a measured oil temperature conversion means to decide that there is an abnormal condition if a preset oil temperature is exceeded,
    wherein the first equation is:

$$\theta oc(t) = \theta_{Ai}(t) + \theta mi(t) \qquad (1)$$

where θoc (t) [° C.] is the oil temperature converted value t minutes later which is an output value from the oil temperature calculation means;

$\theta_{Ai}$ (t) is a virtual ambient temperature; and
$\theta mi$ (t) is an oil temperature rise converted value,
wherein the second equation is:

$$\theta_{Ai}(t) = \sum_{T=0}^{T=n}\left(\left\{1 - e^{-\left[\frac{(T)\times t}{T_A}\right]}\right\} - \left\{1 - e^{-\left[\frac{(T+1)\times t}{T_A}\right]}\right\}\right) \times \theta_A(-Tt) \quad (2)$$

where $T_A$ [minutes] is a time constant of an oil temperature with respect to the ambient temperature;
$\theta_A$ (−nt) [° C.] is an ambient temperature n×t minutes earlier;
t [minutes] is a monitoring interval; and
n is a number of past measurements used for calculation,
wherein the third equation is:

$$\theta mi(t) = \sum_{T=0}^{T=n}\left(\left\{1 - e^{-\left[\frac{(T)\times t}{Tm}\right]}\right\} - \left\{1 - e^{-\left[\frac{(T+1)\times t}{Tm}\right]}\right\}\right) \times \theta mu(-Tt) \quad (3)$$

where Tm [minutes] is a time constant of an oil temperature with respect to a total loss; and
$\theta mu(-nt)$ [K] is an oil temperature rise n×t minutes earlier in a steady state at a load factor of m %,
wherein the fourth equation is:

$$\theta mu(-nt) = \theta ou \times \left[\frac{Wi + Wc \times \left(\frac{m(-nt)}{100}\right)^2}{Wi + Wc}\right]^k \quad (4)$$

where $\theta ou$ [K] is an oil temperature rise in a steady state at a rated (100%) load;

m(−nt.) [%] is an instantaneous load factor n×t minutes earlier;
Wi [W] is a no-load loss;
Wc [W] is a load loss at the rated (100%) load; and
k is a constant,
wherein the fifth equation is:

$$m(-nt) = \frac{i(-nt)}{Is} \times 100(\%) \quad (5)$$

where i (−nt) [A] is a secondary instantaneous current n×t minutes earlier; and
Is [A] is a secondary rated current, and
wherein the sixth equation is:

$$Is = \frac{P}{Es} \times \frac{1}{\sqrt{F}} \quad (6)$$

where Es [V] is a secondary rated voltage;
P [kVA] is a transformer rated capacity; and
F [phase] is the number of transformer phases.

2. The transformer monitoring system according to claim 1,
wherein the oil temperature rise $\theta mu(-nt)$ is 20 Kelvin as an instantaneous oil temperature rise.

3. The transformer monitoring system according to claim 1,
wherein the oil temperature converted value is a close approximation to a measured oil temperature.

* * * * *